United States Patent [19]
Duch

[11] Patent Number: 5,996,581
[45] Date of Patent: Dec. 7, 1999

[54] ENDOTRACHEAL TUBE HOLDER

[76] Inventor: Dyana L. Duch, 220 E. Perimeter Dr., San Antonio, Tex. 78227

[21] Appl. No.: 09/042,420

[22] Filed: Mar. 13, 1998

[51] Int. Cl.$^6$ .............................. A62B 18/02; A62B 18/08
[52] U.S. Cl. ................................ 128/206.26; 128/206.26; 128/206.21; 128/206.24
[58] Field of Search ........................ 128/207.15, 207.17, 128/912, 206.21, 206.24, 206.26

[56] References Cited

U.S. PATENT DOCUMENTS

| | | | |
|---|---|---|---|
| 4,305,387 | 12/1981 | Reist-Kundig et al. | 128/206.26 |
| 5,560,354 | 10/1996 | Berthon-Jones et al. | 128/206.24 |
| 5,660,174 | 8/1997 | Jacobelli | 128/206.24 |

OTHER PUBLICATIONS

Dunleap, Elizabeth, Safe and Easy Ways to Secure Brething Tubes, RN: 26–27, Auustg 1987.
Kaplow, Robert et al., A Comparison of Four Endotracheal Tube Holders, Heart & Lung 23: 59–66, Feb. 1994.
Levy, Howard et al., A Comparative Study of Oral Endotracheal Tube Securing Methods, Chest 104: 1537–40, Nov. 1993.
Tasota, Frederick J. et al., Evaluation of Two Methods Used to Stabilize Oral Endotracheal Tubes, Heart & Lung 16: 140–46, Mar. 1987.

*Primary Examiner*—John G. Weiss
*Assistant Examiner*—Todd Martin
*Attorney, Agent, or Firm*—Wayne J. Colton, Inc.

[57] ABSTRACT

An improved endotracheal tube holder generally comprises an elliptically shaped base member having associated therewith an endotracheal tube stabilization mechanism, for fixing an endotracheal tube into a set position, and an appliance securing mechanism, for affixing the tube holder to a patient's head and/or neck. The tube holder is also provided with a plurality of alternately inflatable fluid chambers, perimetrically disposed about the lower circumference of the holder's base member and oriented for interposition between the base member and the patient's oral and/or facial regions. A source of pressurized fluid is provided for alternately inflating the fluid chambers according to the state of a provided selection device. The improved holder relieves the interface pressure between the base member and the patient's oral and/or facial regions created by the appliance securing mechanism. As a result, the improved endotracheal tube holder provides the benefits associated with tube holding appliances without the concomitant disadvantages of skin deterioration previously associated therewith.

20 Claims, 3 Drawing Sheets

ENDOTRACHEAL TUBE HOLDER

FIELD OF THE INVENTION

The present invention relates to airway management for critical care patients. More particularly, the invention relates to an improved endotracheal tube holder adapted to periodically relieve the interface pressure adjacent the patient's oral and facial regions while securely stabilizing the airway, thereby concurrently addressing skin complication management and effective airway stabilization.

BACKGROUND OF THE INVENTION

Critical care patients often cannot breathe naturally and thus require positive pressure mechanical ventilation to artificially sustain breathing. In the typical treatment regimen, the patient requiring mechanical ventilation is intubated by inserting an endotracheal tube, or airway, through the mouth and into the trachea. The proximal end of the tube is then placed in fluid communication with a mechanical ventilator via an interposed T-fitting whereby positive airflow is provided for inspiration of the patient's lungs.

In order to ensure non-preferential airflow to each lung, the distal end of the endotracheal tube must terminate above the patient's carina of trachea. It is also important, in order to prevent injury, that the tube's distal end terminates below the patient's larynx. Because significant force is applied during ventilation of the patient, however, endotracheal tubes can accidentally become displaced or dislodged, often leading to inadvertent right mainstream bronchus intubation or accidental extubation. As a result of these well-recognized and potentially fatal complications, much attention has been devoted to the study of endotracheal intubation and, in particular, to the search for better methods for securely stabilizing a properly inserted airway.

The clinical standard methods for securing oral endotracheal tubes in non-burn patients have traditionally called for placing either adhesive tape or some type of strap on the tube and affixing it to the patient's face. Unfortunately, these seemingly simple methods often involve complicated techniques to ensure tube stabilization and are often associated with excoriation complications, such as abrasion or break in tissue integrity, in the patient's mouth, lip and facial regions. Because the intubation tends to result in failure to clear normal salivation, the moistened tape holding the tube often loosens, especially when exacerbated by also commonly present coughing and/or gag reflexes. This further contributes to the denuding of the skin, as the frequently loosened tape must usually be removed and replaced.

Of more serious concern, once the tape is loosened, the endotracheal tube is largely free to dislocate or dislodge, presenting serious risk to the patient. In addition to the risk incident tube displacement, any movement of the tube can potentially greatly increase the costs associated with critical care patient management. Reinsertion or repositioning of an endotracheal tube calls for physician intervention according to the majority of critical care hospital protocols. Added to the expense of an otherwise unnecessary physician intervention, most protocols also call for radiographic verification of tube displacement or of proper tube placement following reinsertion or repositioning, or of both. Such radiographic intervention not only increases critical care costs, it unnecessarily exposes the already acutely ill patient to the cumulative effects of X-rays if otherwise preventable. Finally, but further complicating airway management, repeated reinsertion of an endotracheal tube tends to become increasingly difficult due to laryngeal edema or spasms, potentially exacerbating all of the foregoing complications.

In recent years, clinicians have responded to disadvantages associated with taping methods by introducing various appliances that positively engage the endotracheal tube and are adapted to be securely affixed to the patient's head through harness-type arrangements. The typical appliance comprises a hardened plastic mouthpiece, usually specifically adapted to hold the tube, which is secured against the patient's oral and/or facial regions by fabric straps about the head and/or neck. These well-known tube holders have generally shown increased efficacy toward tube stability and decreased short-term occurrences of skin complication.

While most studies of short-term, e.g. four days or less, intubations show less skin deterioration associated with tube holders than with the traditional taping methods, the result is not generally extendable to longer duration intubations. Although most critical care protocols call for tracheostomy in those patients expected to require very long duration mechanical ventilation, many long-term critical care patients nonetheless receive mechanical ventilation through an oral airway because of the difficulty in predicting the duration of required ventilation. As a consequence, long-term critical care patients often inadvertently become exposed to complications of extended oral mechanical ventilation in spite of existing protocol. The hardened plastic mouthpiece, even when padded, generates a significant interface pressure against the patient's oral and/or facial regions when adequately secured. As a result, the longer-term patient typically develops ulceration or pressure sores, often leading to infection and/or necrosis of tissues, in the oral and/or facial regions. Because these advanced skin complications are generally considered far more severe than those typically associated with taping methods, the longer duration critical care patient is often transitioned back to taping methods for stabilization of the endotracheal tube.

Transition back to taping methods unfortunately places the patient at significantly increased risk for complications associated with tube dislocation and accidental extubation. Notwithstanding the seriousness of tube dislocation and accidental extubation, and the enormous effort heretofore expended toward improving airway management, most researchers have all but conceded that no best method may exist. The general consensus rather concludes that a tradeoff between keeping the tube in place and effectively managing complications of the skin must be made. In stark contrast to this state of the art, it is an overriding object of the present invention to improve upon the prior art by providing a method and apparatus whereby complications of the skin in the oral and facial regions may be effectively managed without sacrificing stability in tube placement, in patients requiring extended periods of intubation as well as those intubated for normally expected duration.

It is a further object of the present invention to provide such an improved endotracheal tube holder which allows open access to the patient's mouth for oral hygiene, provides maximum patient comfort and is easy to use.

It is another object of the present invention to provide such an improved endotracheal tube holder which contributes to an overall reduction in the costs generally associated with critical care patient management, such as those resultant physician intervention and radiographic services, while nonetheless contributing to improved overall patient outcome.

It is yet another object of the present invention to provide such an improved endotracheal tube holder which is compact in size, reducing as much as possible the emotional trauma experienced by the critical care patient's family upon viewing the complex of treatment modalities generally required in the critical care scenario.

Finally, many other objects of the present invention will be apparent to those of ordinary skill in the relevant arts in light of the foregoing discussion and the following drawings, exemplary detailed description and appended claims.

SUMMARY OF THE INVENTION

In accordance with the foregoing objects, the present invention—an improved endotracheal tube holder—generally comprises a perimetrically shaped base member for holding an endotracheal tube. The base member is adapted for securement to a patient. It further comprises at least a first and a second, but preferably four or more, fluid chambers disposed about its perimeter and oriented toward the patient when it is secured thereto. The fluid chambers are alternately inflatable to intermittently relieve the interface pressure created between the base member and the patient's oral and/or facial regions when the base member is secured to the patient.

In at least one embodiment, a stopcock valve is utilized to select which fluid chambers should be inflated, whereafter the selected fluid chambers are inflated manually or automatically. In another embodiment, an automated valve and mechanical pump are utilized making the tube holder ideally suited for the incorporation of breathable fabrics, such as the trademark "GORE-TEX," in the inflatable fluid chambers. This greatly contributes to the skin care management aspects of the present invention.

In at least one other embodiment of the present invention, a tube stabilization mechanism is provided for releasably engaging an endotracheal tube. This mechanism preferably comprises a cinch for easily engaging the tube and a release mechanism for easily releasing the cinch from the tube.

Finally, many other features and advantages of the present invention will be apparent to those of ordinary skill in the relevant arts, especially in light of the foregoing discussions and the following drawings, exemplary detailed description and appended claims.

BRIEF DESCRIPTION OF THE DRAWINGS

Although the scope of the present invention is much broader than any particular embodiment, a detailed description of the preferred embodiment follows together with illustrative figures, wherein like reference numerals refer to like components, and wherein.

DETAILED DESCRIPTION OF THE PREFERRED EMBODIMENT

Figure 1:
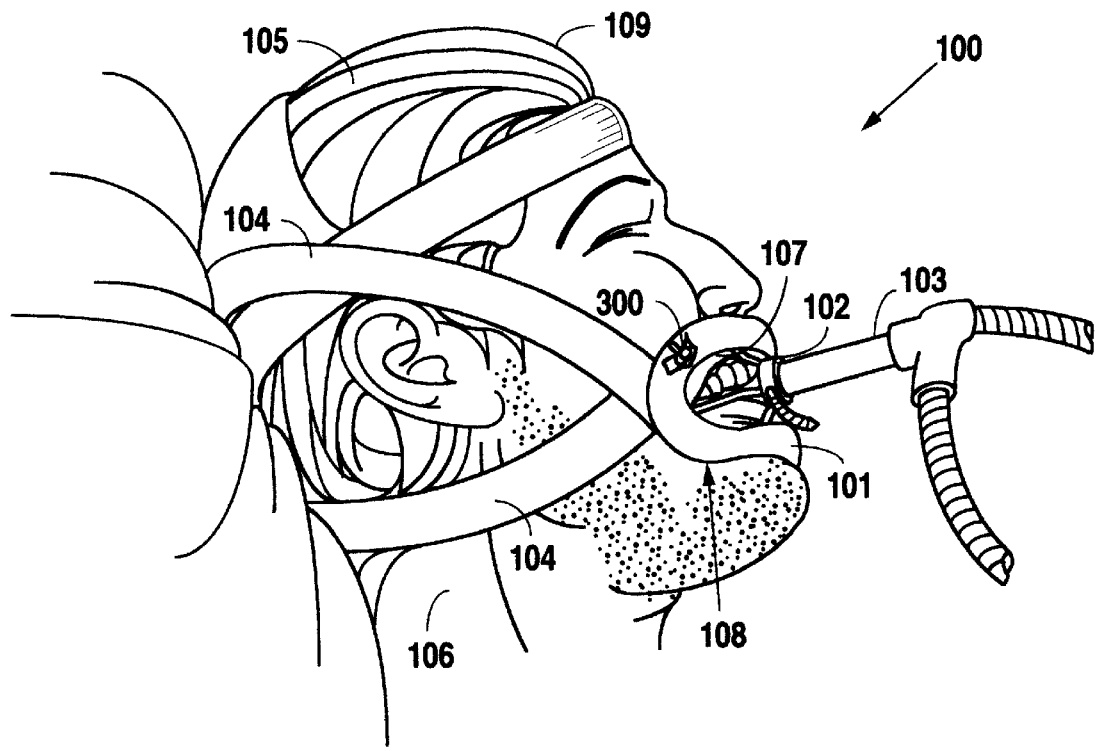
FIG. 1 shows, in perspective view, the improved endotracheal tube holder 100 of the present invention as operable upon a mechanically ventilated critical care patient 109.

Although those of ordinary skill in the art will readily recognize many alternative embodiments, especially in light of the illustrations provided herein, this detailed description is exemplary of the preferred embodiment of the present invention—an improved endotracheal tube holder 100, the scope of which is limited only by the claims appended hereto.

According to the preferred embodiment of the present invention, as shown in FIGS. 1 through 6, an improved endotracheal tube holder 100 generally comprises an elliptically shaped base member 101 having associated therewith an endotracheal tube stabilization mechanism 102, for fixing an endotracheal tube 103 into a set position, and an appliance securing mechanism 104, for affixing the tube holder 100 to a patient's head 105 and/or neck 106. The tube holder 100 is also provided with a plurality of alternately inflatable fluid chambers 200, 201, perimetrically disposed about the lower circumference 202 of the holder's base member 101 and oriented for interposition between the base member 101 and the patient's oral 107 and/or facial 108 regions. A source of pressurized fluid 301, 600 is provided for alternately inflating the fluid chambers 200, 201 according to the state of a provided selection device 300, 601.

In the preferred method of the present invention, as will be better understood further herein, the patient 109 is first intubated with an endotracheal tube 103 as known to those of ordinary skill in the art. Once the tube 103 is properly positioned, the improved tube holder 100 is placed on the critical care patient 109, with at least some of the fluid chambers 200, 201 in their inflated state, and affixed with the appliance securing mechanism 104. The properly positioned endotracheal tube 103 is then securely stabilized with the tube stabilization mechanism 102. Finally, the fluid chambers 200, 201 are alternately inflated from the pressurized fluid source 301, 600, according to the state of the selection device 300, 601, in order to facilitate and promote circulation within the patient's oral 107 and/or facial 108 regions.

Figure 2:
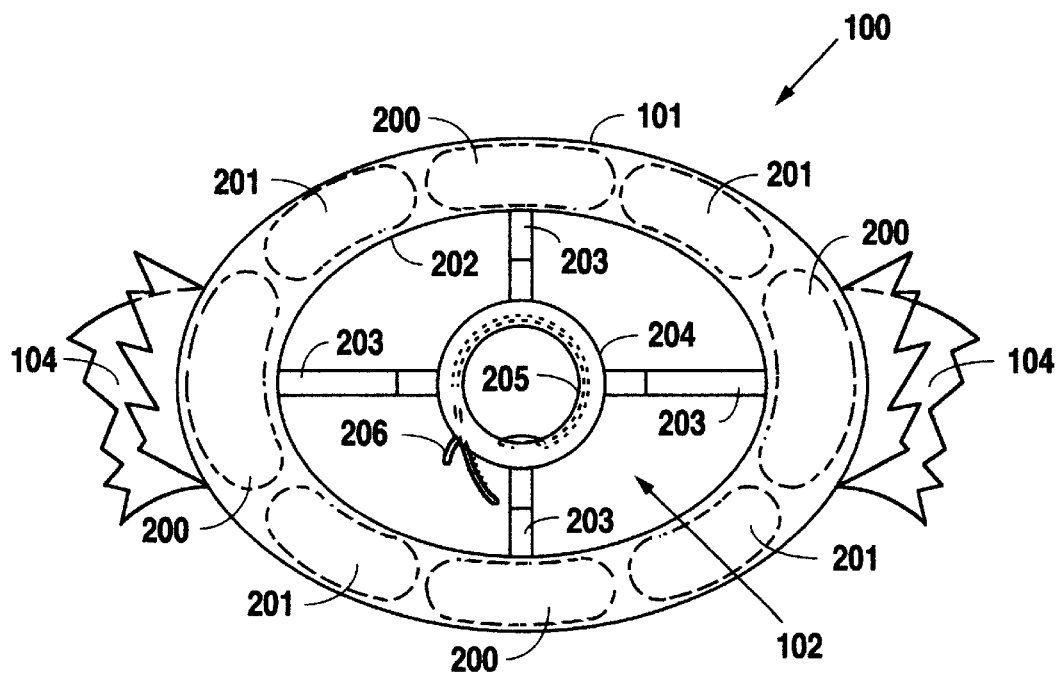
FIG. 2 shows, in top plan view, the improved endotracheal tube holder 100 of the present invention.
Figure 3:
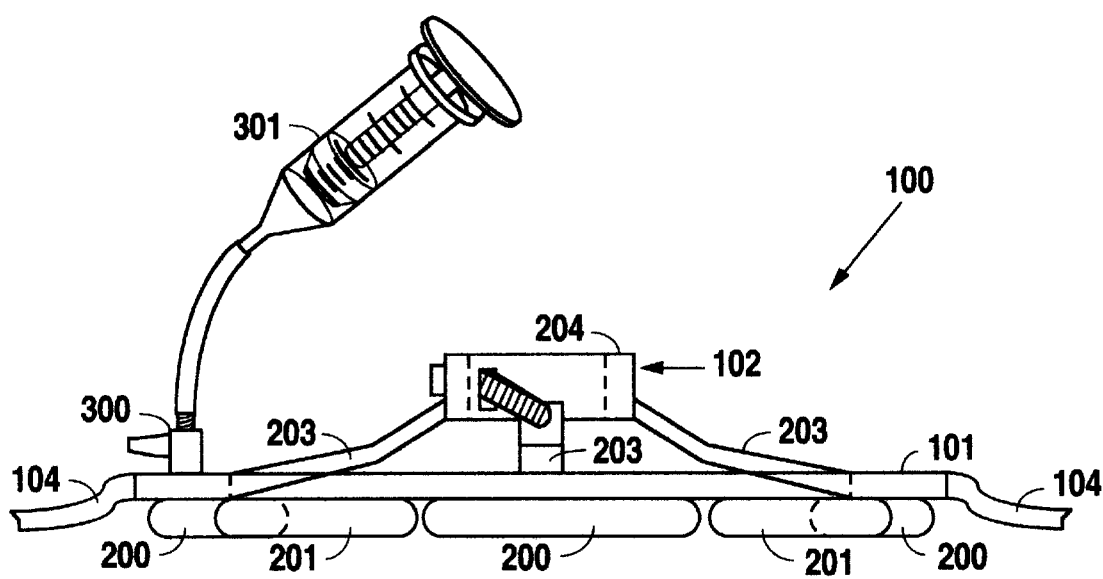
FIG. 3 shows, in side plan view, the improved endotracheal tube holder 100 of the present invention, including the syringe embodiment of the pressurized fluid source 301.

Referring now particularly to FIGS. 2 and 3, the base member 101 of the endotracheal tube holder 100 is preferably shaped in the form of a substantially flat, open ellipse of appropriate size to fully contain, within the open area, the patient's oral region 107 without extending to the chin or nose. The base member 100 is preferably constructed of hard plastic, although those of ordinary skill in the art will recognize the many possible alternatives. The appliance securing mechanism 104, which in the preferred embodiment comprises fabric straps with releasably engageable hook and loop type fasteners, is conventionally secured to the base member 101 in any one of many known manners. In order to promote maximum access to the patient's oral region 107, the tube stabilization mechanism 102 is preferably dependently attached to the base member 101 with a small plurality of thin, plastic strips 203, which may be formed integral with either the base member 101 or the stabilization mechanism 102, or both. In choosing the widths of the strips 203, as will be appreciated by those of ordinary skill in the art, a balance should be drawn between the need for rigidity in the strips 203 and the desire for maximum open area through the central region of the base member 101.

Figure 4:
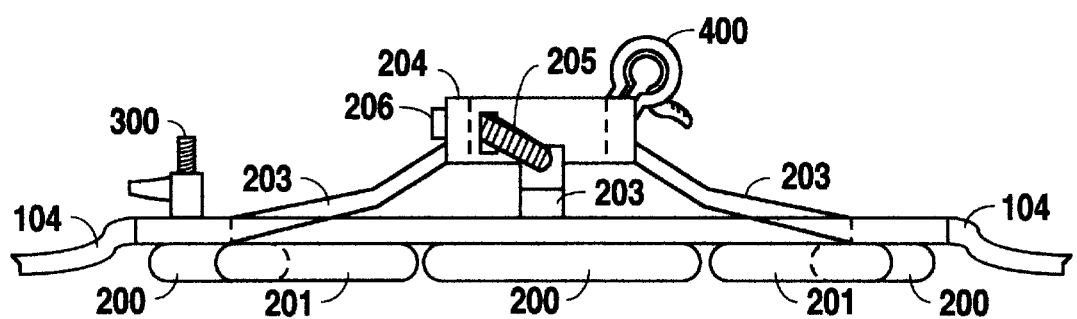
FIG. 4 shows, in side plan view, the improved endotracheal tube holder 100 of the present invention, with an optional device 400 for use in either nasal intubation or enteral feeding.

As also best shown in FIGS. 2 and 3, the endotracheal tube stabilization mechanism 102 generally comprises a short, tubular section 204, preferably constructed of hard plastic, suspended over the central region of the base member 101. While those of ordinary skill in the art will recognize that it is not necessary that the tubular section 204 of the stabilization mechanism 102 be raised from the base member 101, failure to do so will result in decreased access to the patient's oral region 107 for inspection and/or hygiene. The tubular section 204 further comprises an integral cinch 205, with release mechanism 206, for immobilizing an endotracheal tube 103, inserted therethrough and releasing the same. While those of ordinary skill in the art recognize many alternative embodiments for immobilizing the tube 103, it is considered critical that the chosen embodiment be operable by the caregiver with minimum effort in order to prevent accidental tube dislocation during operation of the mechanism 102. As shown in FIG. 4, an alternative embodiment comprises the addition and/or substitution of a stabilizer 400 adapted for use in nasal intubation.

Figure 5:
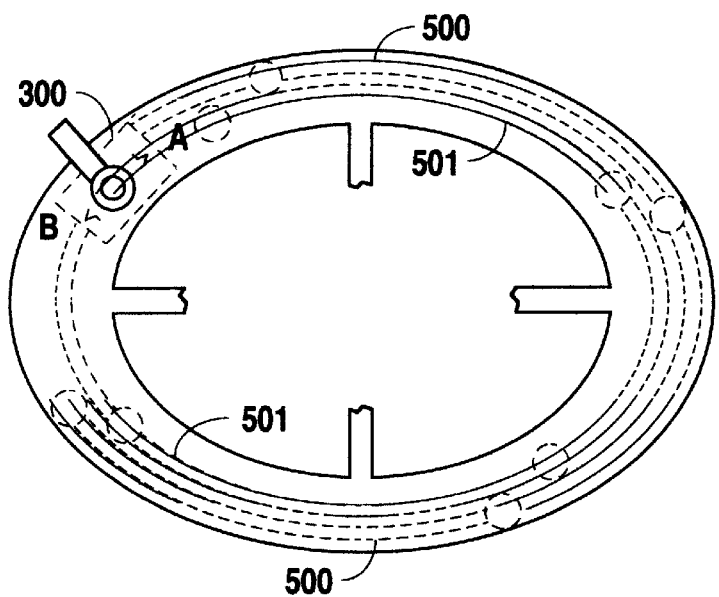
FIG. 5 shows, in top plan view, the manifold plumbing for delivering pressurized fluid to the inflatable fluid chambers 200, 201 of the improved endotracheal tube holder 100 of the present invention.
Figure 6:
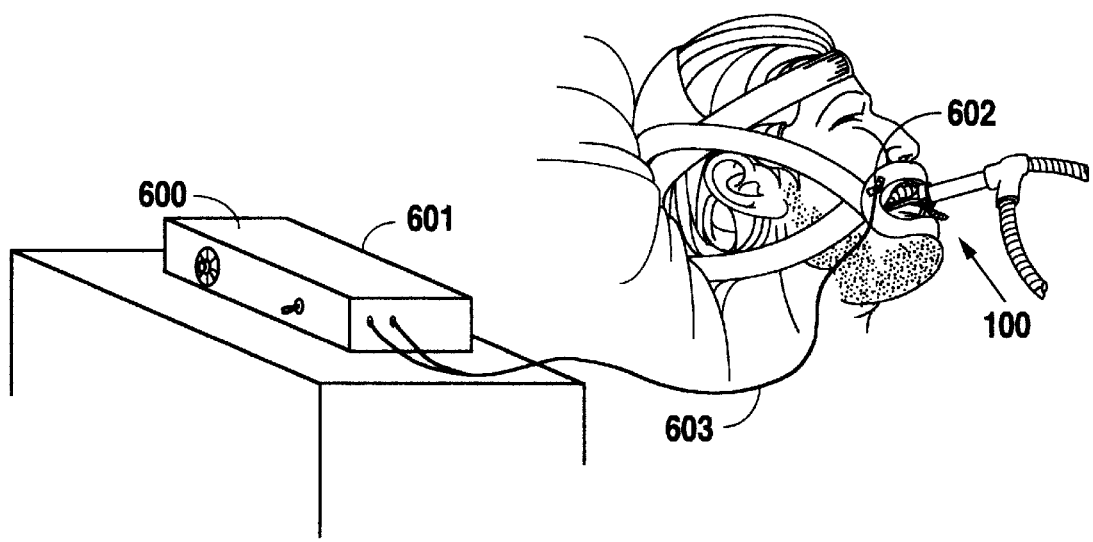
FIG. 6 shows, in perspective view, the improved endotracheal tube holder 100 of the present invention, including the mechanical pump embodiment of the pressurized fluid source 600.

Referring again to FIGS. 2 and 3, the inflatable fluid chambers 200, 201 are shown to be disposed about the circumference 202 of the base member 101. As will be better understood further herein, the chambers are preferably divided into a first set and a second set, wherein the chambers 201 of the second set are individually interposed between the chambers 200 of the first set. As shown in FIGS. 3 and 5, a selection device 300 provides an interconnection between a source of pressurized fluid 301, which in the preferred embodiment comprises a simple syringe, and the inflatable chambers 200, 201. A first manifold 500, preferably embedded within the base member 101, provides fluid communication from the selection device 300 to the chambers 200 of the first set. Likewise, a second manifold 501, also preferably embedded within the base member 101, provides fluid communication from the selection device 300 to the chambers 201 of the second set. Depending upon the state of the selection device 300, which in the preferred embodiment of the present invention comprises a three position stopcock, fluids may communicate between the source 301 and the first set of chambers 200, between the source 301 and the second set of chambers 201, or not at all.

In the embodiment depicted in FIG. 3, the fluid chambers 200, 201 preferably comprise a resilient, airtight material such as soft plastic, in order to prevent deflation of the chambers 200, 201 in the absence of the pressurized fluid source 301. In an alternative embodiment, shown in FIG. 6, a mechanical pump 600 is utilized as the source of pressurized fluid. In this embodiment, the selection device 601 is automated and preferably placed within the pump 600 for directly providing pressurized fluid to the two sets of chambers 200, 201 via a dual conduit 603. In this embodiment, where the pressurized source 600 may be intermittently applied to the chambers 200, 201, the chambers 200, 201 preferably comprise an air and water impermeable, but vapor permeable, nylon mesh weave material, such as that readily available from W. L. Gore and Associates under the well-known trademark "GORE-TEX." This material is recognized by those of ordinary skill in the art as contributing to skin care management by preventing moisture buildup on the skin thereby reducing softening of the skin.

In operation, the patient 109 is first intubated with an endotracheal tube 103 as known to those of ordinary skill in the art. Once the tube 103 is properly positioned, the improved tube holder 100 is placed on the critical care patient 103, with at least some of the fluid chambers 200, 201 in their inflated state, and affixed with the appliance securing mechanism 104. The properly positioned endotracheal tube 103 is then securely stabilized with the tube stabilization mechanism 102 by pulling tight the provided cinch 205. Finally, the fluid chambers 200, 201 are alternately inflated from the pressurized fluid source 301, 600, according to the state of the selection device 300, 601, in order to facilitate and promote circulation within the patient's oral 107 and/or facial 108 regions. When the chambers 200 of the first set are inflated, the chambers 201 of the second set are deflated, and vice-versa. In this manner, the improved tube holder 100 is always held snuggly against the patients oral 107 and/or facial 108 regions, but never in any one area of these regions for more than one cycle of inflation and deflation. As a result, free circulation is enabled in the areas of the deflated chambers while the alternate chambers hold fast the endotracheal tube 103. The result of the present invention is thus an improved endotracheal tube holder 100 adapted to periodically relieve the interface pressure adjacent the patient's oral 107 and facial 108 regions while securely stabilizing the airway 103, thereby concurrently addressing skin complication management and effective airway stabilization.

While the foregoing description is exemplary of the preferred embodiment of the present invention, those of ordinary skill in the relevant arts will recognize the many variations, alterations, modifications, substitutions and the like as are readily possible, especially in light of this description, the accompanying drawings and claims drawn thereto. For example, in the embodiment of FIG. 4, the additional tubular section 400 may be adapted to hold a nasogastric tube for enteral feeding of the ventilated patient 109. In any case, because the scope of the present invention is much broader than any particular embodiment, the foregoing detailed description should not be construed as a limitation of the scope of the present invention, that being limited only by the claims appended hereto.

What is claimed is:

1. An endotracheal tube holder, comprising:
   a base member for holding an endotracheal tube, said base member being adapted for securement to a patient; and
   at least a first and a second fluid chamber adjacent to said base member and oriented toward the patient when said base member is secured thereto, said first and second fluid chambers being alternately inflatable.

2. The endotracheal tube holder as recited in claim 1, wherein said base member is adapted for perimetric disposition about the patient's mouth.

3. The endotracheal tube holder as recited in claim 2, comprising at least four fluid chambers disposed about the perimeter of said base member and oriented toward the patient when said base member is secured thereto, at least two of said chambers being in fluid communication with each other as a first set and at least two other of said chambers being in fluid communication with each other as a second set.

4. The endotracheal tube holder as recited in claim 3, further comprising a pneumatic switch for selectively enabling inflation of said first and second sets of fluid chambers.

5. The endotracheal tube holder as recited in claim 4, wherein each fluid chamber of said second set is interposed one each between the fluid chambers of said first set.

6. The endotracheal tube holder as recited in claim 4, wherein said pneumatic switch comprises a stopcock.

7. The endotracheal tube holder as recited in claim 6, wherein each said fluid chamber comprises a substantially airtight material.

8. The endotracheal tube holder as recited in claim 4, wherein said pneumatic switch comprises an automatically actuated valve.

9. The endotracheal tube holder as recited in claim 8, wherein each said fluid chamber comprises a substantially air and water impermeable, vapor permeable material.

10. The endotracheal tube holder as recited in claim 9, wherein each said fluid chamber further comprises a nylon mesh weave material.

11. The endotracheal tube holder as recited in claim 1, wherein said base member further comprises a tube stabilization mechanism, said tube stabilization mechanism being adapted to releasably engage an endotracheal tube.

12. The endotracheal tube holder as recited in claim 11, wherein said tube stabilization mechanism comprises:
  a cinch for engaging an endotracheal tube; and
  a release mechanism for releasing said cinch from the endotracheal tube.

13. A system for holding an endotracheal tube, comprising:
  a base member for holding an endotracheal tube, said base member being adapted for securement to a patient;
  a least a first and a second fluid chamber adjacent to said base member and oriented toward the patient when said base member is secured thereto, said first and second fluid chambers being alternately inflatable; and
  a source of pressurized fluid, in communication with said first and second fluid chambers, for intermittently inflating said first and second fluid chambers.

14. The system for holding an endotracheal tube as recited in claim 13, wherein said source of pressurized fluid comprises a syringe.

15. The system for holding an endotracheal tube as recited in claim 13, wherein said source of pressurized fluid comprises a mechanical pump.

16. The system for holding an endotracheal tube as recited in claim 15, further comprising an automated selector, in communication with said mechanical pump, for alternating inflation of said first fluid chamber and said second fluid chamber.

17. A method for stabilizing an endotracheal tube, comprising the steps of:
  placing a base member proximate to the endotracheal tube of an intubated patient;
  securing said base member to the patient, creating an interface pressure between said base member and the patient;
  securing the endotracheal tube to said base member, thereby substantially stabilizing the endotracheal tube with respect to said base member; and
  intermittently relieving said interface pressure between said base member and the patient.

18. The method for stabilizing an endotracheal tube as recited in claim 17, wherein said intermittently relieving step comprises:
  deflating a first inflatable chamber between said base member and the patient; and
  inflating a second inflatable chamber between said base member and the patient.

19. The method for stabilizing an endotracheal tube as recited in claim 17, wherein said intermittently relieving step comprises:
  deflating a first set of inflatable chambers between said base member and the patient; and
  inflating a second set of inflatable chambers between said base member and the patient.

20. The method for stabilizing an endotracheal tube as recited in claim 19, wherein:
  said base member is adapted for perimetric disposition about the patient's mouth, and
  each inflatable chamber of said first and second sets is disposed about the perimeter of said base member, the chambers of said second set being interposed one each between the chambers of said first set.

* * * * *